US012708310B2

(12) United States Patent
Zimmerman et al.

(10) Patent No.: US 12,708,310 B2
(45) Date of Patent: Aug. 18, 2026

(54) TRANSLATING AI ALGORITHMS FROM 12-LEAD CLINICAL ECGS TO PORTABLE AND CONSUMER ECGS WITH FEWER LEADS

(71) Applicant: Tempus AI, Inc., Chicago, IL (US)

(72) Inventors: Noah Zimmerman, Chicago, IL (US); Joel Dudley, Chicago, IL (US); Marcus Badgeley, Chicago, IL (US); Will Thompson, Chicago, IL (US); Greg Lee, Chicago, IL (US); Kipp Johnson, Chicago, IL (US); Arun Nemani, Chicago, IL (US)

(73) Assignee: TEMPUS AI, INC., Chicago, IL (US)

( * ) Notice: Subject to any disclaimer, the term of this patent is extended or adjusted under 35 U.S.C. 154(b) by 0 days.

(21) Appl. No.: 17/814,229

(22) Filed: Jul. 21, 2022

(65) Prior Publication Data

US 2023/0028783 A1 Jan. 26, 2023

Related U.S. Application Data

(60) Provisional application No. 63/224,841, filed on Jul. 22, 2021.

(51) Int. Cl.
*A61B 5/327* (2021.01)
*A61B 5/00* (2006.01)
*A61B 5/333* (2021.01)

(52) U.S. Cl.
CPC .............. *A61B 5/333* (2021.01); *A61B 5/327* (2021.01); *A61B 5/7267* (2013.01); *A61B 5/7275* (2013.01)

(58) Field of Classification Search
None
See application file for complete search history.

(56) References Cited

U.S. PATENT DOCUMENTS 11,576,623 B2 * 2/2023 Biswas .............. A61B 5/02416
2009/0306485 A1 12/2009 Bell (Continued)

FOREIGN PATENT DOCUMENTS

CN 112932499 A 6/2021
EP 4162876 A1 * 4/2023
WO WO-2022014943 A1 * 1/2022

OTHER PUBLICATIONS

JeeEun Lee et al., "Synthesis of Electrocardiogram V-Lead Signals From Limb-Lead Measurement Using R-Peak Aligned Generative Adversarial Network," in IEEE Journal of Biomedical and Health Informatics, vol. 24, No. 5, pp. 1265-1275, May 2020, doi: 10.1109/JBHI.2019.2936583, viewed on Sep. 27, 22.*

(Continued)

*Primary Examiner* — Unsu Jung
*Assistant Examiner* — James Moss
(74) *Attorney, Agent, or Firm* — Quarles & Brady LLP

(57) ABSTRACT

A method includes the step of receiving electrocardiogram (ECG) data associated with a plurality of patients and an electrocardiogram configuration including a plurality of leads and a time interval. The electrocardiogram data includes, for each lead included in the plurality of leads, voltage data associated with at least a portion of the time interval. The method also includes training an artificial intelligence model on the ECG data, tuning the artificial intelligence model using data from a device having fewer leads than the plurality of leads, and evaluating the artificial intelligence model on additional data received from the ECG data.

16 Claims, 7 Drawing Sheets

(56) References Cited

U.S. PATENT DOCUMENTS

| | | | | |
|---|---|---|---|---|
| 2014/0288435 | A1* | 9/2014 | Richards | A61B 5/1123 600/479 |
| 2015/0235143 | A1 | 8/2015 | Eder | |
| 2015/0351690 | A1* | 12/2015 | Toth | A61B 5/6839 600/391 |
| 2020/0176122 | A1 | 6/2020 | Teplitzky et al. | |
| 2021/0076960 | A1 | 3/2021 | Fornwalt et al. | |
| 2021/0089921 | A1 | 3/2021 | Aghdasi et al. | |
| 2021/0100471 | A1 | 4/2021 | Yu et al. | |
| 2021/0169392 | A1* | 6/2021 | Albert | H04B 1/385 |
| 2022/0378379 | A1 | 12/2022 | Zimmerman | |
| 2022/0384044 | A1 | 12/2022 | Ulloa-Cerna | |
| 2022/0384045 | A1 | 12/2022 | Zimmerman | |
| 2024/0341661 | A1* | 10/2024 | Kwon | A61B 5/327 |

OTHER PUBLICATIONS

Lee Jaehyeok et al.: "Reconstruction of Precordial Lead Electrocardiogram From Limb Leads Using the State-Space Model", IEEE Journal of Biomedical and Health Informatics, IEEE, vol. 20, No. 3, May 1, 2016 (May 1, 2016), pp. 818-828, DOI: 10.1109/JBHI.2015.2415519, viewed on Sep. 26, 2022.*

Wang Lu-Di et al: "A novel method based on convolutional neural networks for deriving standard 12-lead ECG from serial 3-lead ECG", Frontiers of IT & EE, Zhejiang University Press, vol. 20, No. 3, Apr. 19, 2019 (Apr. 19, 2019), pp. 405-413, DOI: 10.1631 FITEE.1700413, viewed on Sep. 26, 2022.*

Zhang Qingxue et al: "AII-ECG: A Least-number of Leads ECG Monitor for Standard 12-lead ECG Tracking during Motion*", 2019 IEEE Healthcare Innovations and Point of Care Technologies, (Hi-POCT), IEEE, Nov. 20, 2019 (Nov. 20, 2019), pp. 103-106, DOI: 10.1109/HI-POCT45284.2019.8962742, viewed on Sep. 26, 2022.*

Xu Zijian et al: "Reconstruction of 12-Lead Electrocardiogram Based on GVM", 2018 Sixth International Conference On Advanced Cloud and Big Data (CBD), IEEE, Aug. 12, 2018 (Aug. 12, 2018), pp. 275-280, DOI: 10.1109/CBD.2018.00056, viewed on Sep. 26, 2022.*

Hussein Atoui et al: "A Novel Neural-Network Model for Deriving Standard 12-Lead ECGs From Serial Three-Lead ECGs: Application to Self-Care", IEEE Transactions On It in Biomedicine, vol. 14, No. 3, May 1, 2010 (May 1, 2010), pp. 883-890 ,DOI: 10.1109/TITB.2010.2047754, viewed on Sep. 26, 2022.*

Joon-Myoung Kwon et al. Deep Learning-Based Algorithm for Detecting Aortic Stenosis Using Electrocardiography. Mar. 21, 2020. https://doi.org/10.1161/JAHA.119.014717. J Am Heart Assoc. 2020;9:e014717. DOI: 10.1161/JAHA/119.14717, viewed on Sep. 26, 2022.*

Tomer Golany et al. (2020). Improving ECG Classification Using Generative Adversarial Networks. Proceedings of the AAAI Conference on Artificial Intelligence, 34(08), 13280-13285. https://doi.org/10.1609/aaai.v34i08.7037. viewed on Sep. 27, 2022.*

I. Tomašić et al., "Electrocardiogramastems With Reduced Numbers of Leads—Synthesis of the 12-Lead ECG," in IEEE Reviews in Biomedical Engineering, vol. 7, pp. 126-142, 2014, doi: 10.1109/RBME.2013.2264282.*

H. Atoui et al., "A neural network approach for patient-specific 12-lead ECG synthesis in patient monitoring environments," Computers in Cardiology, 2004, Chicago, IL, USA, 2004, pp. 161-164, doi: 10.1109/CIC.2004.1442896.*

Dongdong Zhang et al., Interpretable deep learning for automatic diagnosis of 12-lead electrocardiogram, iScience, vol. 24, Issue 4, 2021, 102373, ISSN 2589-0042, https://doi.org/10.1016/j.isci.2021.102373, viewed on Nov. 28, 2023. (Year: 2021).*

Chih-Hao Hsu et al., "Robust signal synthesis of the 12-lead ECG using 3-Lead wireless ECG systems," 2014 IEEE International Conference on Communications (ICC), Sydney, NSW, Australia, 2014, pp. 3517-3522, doi: 10.1109/ICC.2014.6883866, viewed on Nov. 28, 2023. (Year: 2014).*

Jacob Gildenblat, Pruning deep neural networks to make them fast and small, Aug. 22, 2019, https://web.archive.org/web/20190822211756/https://jacobgil.github.io/deeplearning/pruning-deep-learning, viewed on Aug. 19, 2024 (Year: 2019).*

Apple Inc., De Novo Classification Request for ECG App, 2018, 15 pages.

Weimann et al., Transfer Learning for ECG Classification, Scientific Reports, 2021, 11:5251, pp. 1-12.

PCT International Search Report and Written Opinion, PCT/US2022/074031, Oct. 24, 2022, 9 pages.

Jo, Yong-Yeon, and Joon-Myoung Kwon. "ECGT2T: Electrocardiogram synthesis from Two asynchronous leads to Ten leads." CoRR (2021).

Extended European Search Report in European Application No. 22846845.0; received on Apr. 11, 2025.

* cited by examiner

TRANSLATING AI ALGORITHMS FROM 12-LEAD CLINICAL ECGS TO PORTABLE AND CONSUMER ECGS WITH FEWER LEADS

CROSS-REFERENCE TO RELATED APPLICATIONS

This application claims the benefit of U.S. Provisional Application No. 63/224,841 filed Jul. 22, 2021, and titled "Translating AI Algorithms from 12-Lead Clinical ECGS to Portable and Consumer ECGS with Fewer Leads," which is incorporated herein by reference in its entirety.

U.S. Provisional Application No. 63/202,436, filed Jun. 10, 2021, and titled "ECG Based Future Atrial Fibrillation Predictor Systems and Methods," is incorporated herein by reference in its entirety.

STATEMENT REGARDING FEDERALLY SPONSORED RESEARCH OR DEVELOPMENT

Not applicable.

BACKGROUND OF THE DISCLOSURE

The field of the disclosure is predictive ECG testing and more specifically a system and process for translating artificial intelligence algorithms developed to be used with data derived from clinical ECGs using a plurality of leads so that they are usable with data derived from clinical or consumer ECGs using a second, smaller number of leads.

Large datasets with matched ECG and clinical health data come from healthcare providers and are predominantly 10-second 12-lead ECG devices. Portable clinical ECGs and portable consumer devices can collect ECG data more often but are often limited to 1 or a few leads. Additionally, manufacturers of those consumer devices do not naturally possess sufficient clinical data in order to directly train health AI models using those devices' data.

ECGs may be used to evaluate a patient to determine whether they are experiencing or have experienced a cardiac event such as atrial fibrillation ("AF"). AF is a cardiac rhythm disorder associated with several important adverse health outcomes including stroke and heart failure. In patients with AF and risk factors for thromboembolism, early anticoagulation has been shown to be effective at preventing strokes. Unfortunately, AF often goes unrecognized and untreated since it is frequently asymptomatic or minimally symptomatic. Thus, systems and methods to screen for and identify undetected AF can assist in preventing strokes.

Population-based screening for AF is challenging for two primary reasons. One, the yearly incidence of AF in the general population is low with reported incidence rates of less than 10 per 1000 person years under the age of 70. Two, AF is often "paroxysmal," with the patient going in and out of AF for periods of time, with many episodes lasting less than 24 hours. Currently, the most common screening strategy is opportunistic pulse palpation, sometimes in conjunction with a 12-lead electrocardiogram during routine medical visits. This has been shown to be cost-effective in certain populations and is recommended in some guidelines. However, studies of implantable cardiac devices have suggested that this strategy will miss many cases of AF.

A number of continuous monitoring devices are now available to detect paroxysmal and asymptomatic AF. Patch monitors can be worn for up to 14-30 days, implantable loop recorders provide continuous monitoring for as long as 3 years, and wearable monitors, sometimes used in conjunction with mobile devices, can be worn indefinitely. Although these devices may provide for substantially continuous monitoring, they still may not be well-suited to detect cardiac events with a high degree of accuracy due to the fact that they have significantly fewer leads than a traditional ECG.

SUMMARY OF THE DISCLOSURE

In one aspect, the present disclosure provides a method to train an AI health model on a large dataset, such as a dataset generated from a multiplicity of patients using a 12-lead clinical ECG device, and then further adapt the model to a device with fewer leads and with far fewer samples.

In another aspect, a method includes the step of receiving electrocardiogram (ECG) data associated with a plurality of patients and an electrocardiogram configuration including a plurality of leads and a time interval. The electrocardiogram data includes, for each lead included in the plurality of leads, voltage data associated with at least a portion of the time interval. The method also includes training an artificial intelligence model on the ECG data, tuning the artificial intelligence model using data from a device having fewer leads than the plurality of leads, and evaluating the artificial intelligence model on additional data received from the ECG data.

Training the artificial intelligence model on the ECG data includes leveraging clinical data associated with the plurality of patients.

Tuning may include isolating a single channel featurization unit based at least in part on its performance, preventing tuning from modifying the single channel featurization unit, and adding new neural layers to the artificial intelligence model after the single channel featurization unit.

In still another aspect, a method includes receiving electrocardiogram data associated with a wearable device and a patient and an electrocardiogram configuration including at least one lead and a time interval, the electrocardiogram data comprising voltage data associated with at least a portion of the time interval. The method also may include receiving a transformed artificial intelligence model, wherein the transformed model is based at least in part on a model trained from electrocardiogram data having two or more leads which has been refined with electrocardiogram data associated with the wearable device and having at least one lead, and wherein the transformed model is trained to generate a label. In addition, the method may include tuning the transformed model using data from the wearable device, and generating a notification based at least in part on the label.

The method may include displaying the notification on a display screen of the wearable device, transmitting an email to the patient including the notification, or transmitting a text message to the patient including the notification or providing the patient with a text message including an HTML link to a webpage including the notification. Additionally or alternatively, the method may include updating an electronic medical record of the patient to include the notification and alerting the patient's physician of the notification or of the update to the electronic medical record.

The label may be a risk score, e.g., where the risk score is indicative of a likelihood the patient will suffer from a cardiac event within a predetermined period of time from when the electrocardiogram data was generated.

The label may be an indication of an event occurring substantially concurrently with the receiving step or an indication of a likelihood of an event occurring substantially concurrently with the receiving step. In either case, the event may be a cardiac event, such as atrial fibrillation.

DETAILED DESCRIPTION OF THE DISCLOSURE

Figure 1:
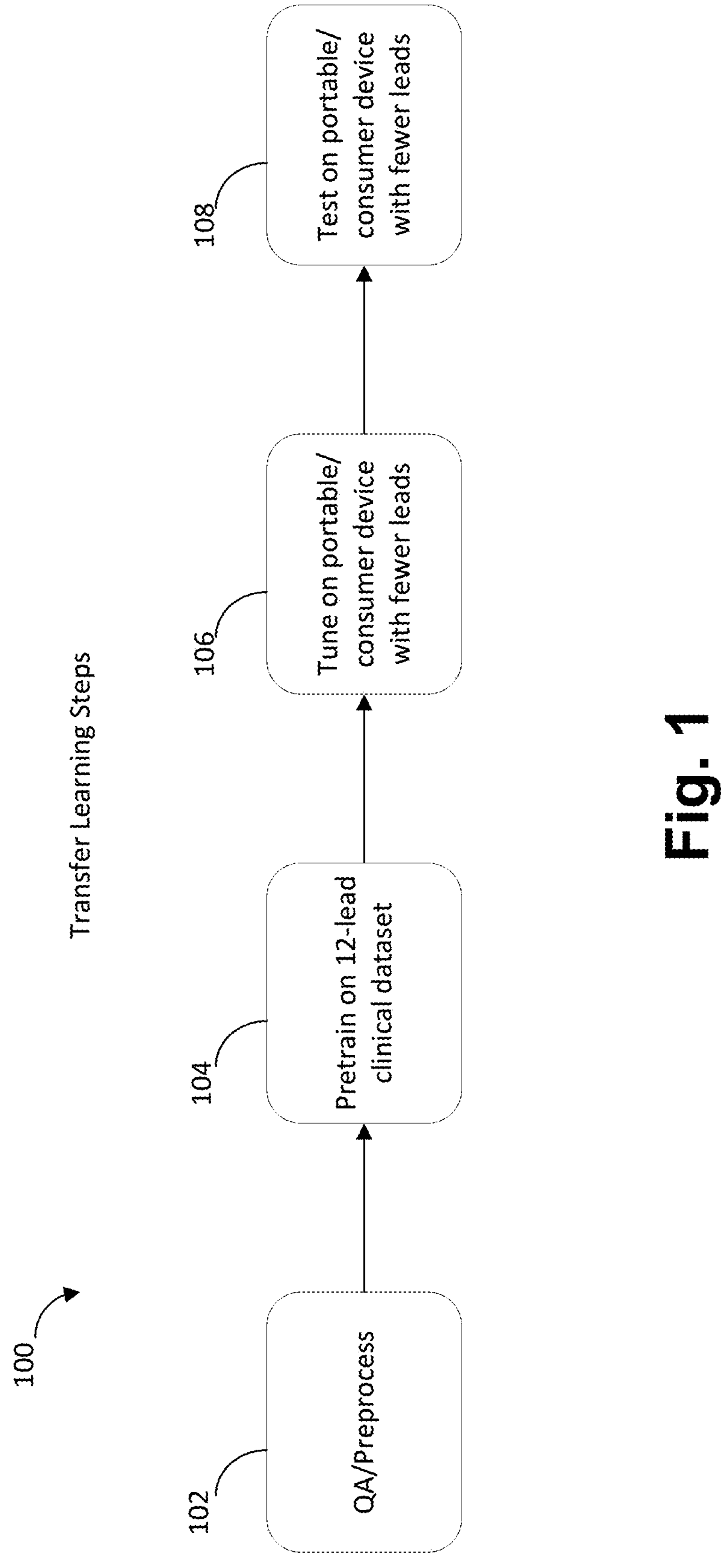
FIG. 1 is an example of a method for translating AI algorithms from multi-lead clinical ECGs to portable and consumer ECGs with fewer leads.

The various aspects of the subject disclosure are now described with reference to the drawings, wherein like reference numerals correspond to similar elements throughout the several views. It should be understood, however, that the drawings and detailed description hereafter relating thereto are not intended to limit the claimed subject matter to the particular form disclosed. Rather, the intention is to cover all modifications, equivalents, and alternatives falling within the spirit and scope of the claimed subject matter.

In the following detailed description, reference is made to the accompanying drawings which form a part hereof, and in which is shown by way of illustration, specific embodiments in which the disclosure may be practiced. These embodiments are described in sufficient detail to enable those of ordinary skill in the art to practice the disclosure. It should be understood, however, that the detailed description and the specific examples, while indicating examples of embodiments of the disclosure, are given by way of illustration only and not by way of limitation. From this disclosure, various substitutions, modifications, additions, rearrangements, or combinations thereof within the scope of the disclosure may be made and will become apparent to those of ordinary skill in the art.

In accordance with common practice, the various features illustrated in the drawings may not be drawn to scale. The illustrations presented herein are not meant to be actual views of any particular method, device, or system, but are merely idealized representations that are employed to describe various embodiments of the disclosure. Accordingly, the dimensions of the various features may be arbitrarily expanded or reduced for clarity. In addition, some of the drawings may be simplified for clarity. Thus, the drawings may not depict all of the components of a given apparatus (e.g., device) or method. In addition, like reference numerals may be used to denote like features throughout the specification and figures.

Information and signals described herein may be represented using any of a variety of different technologies and techniques. For example, data, instructions, commands, information, signals, bits, symbols, and chips that may be referenced throughout the above description may be represented by voltages, currents, electromagnetic waves, magnetic fields or particles, optical fields or particles, or any combination thereof. Some drawings may illustrate signals as a single signal for clarity of presentation and description. It will be understood by a person of ordinary skill in the art that the signal may represent a bus of signals, wherein the bus may have a variety of bit widths and the disclosure may be implemented on any number of data signals including a single data signal.

The various illustrative logical blocks, modules, circuits, and algorithm acts described in connection with embodiments disclosed herein may be implemented as electronic hardware, computer software, or combinations of both. To clearly illustrate this interchangeability of hardware and software, various illustrative components, blocks, modules, circuits, and acts are described generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the embodiments of the disclosure described herein.

In addition, it is noted that the embodiments may be described in terms of a process that is depicted as a flowchart, a flow diagram, a structure diagram, or a block diagram. Although a flowchart may describe operational acts as a sequential process, many of these acts can be performed in another sequence, in parallel, or substantially concurrently. In addition, the order of the acts may be re-arranged. A process may correspond to a method, a function, a procedure, a subroutine, a subprogram, etc. Furthermore, the methods disclosed herein may be implemented in hardware, software, or both. If implemented in software, the functions may be stored or transmitted as one or more instructions or code on a computer-readable medium. Computer-readable media includes both computer storage media and communication media including any medium that facilitates transfer of a computer program from one place to another.

It should be understood that any reference to an element herein using a designation such as "first," "second," and so forth does not limit the quantity or order of those elements, unless such limitation is explicitly stated. Rather, these designations may be used herein as a convenient method of distinguishing between two or more elements or instances of an element. Thus, a reference to first and second elements does not mean that only two elements may be employed there or that the first element must precede the second element in some manner. Also, unless stated otherwise a set of elements may comprise one or more elements.

As used herein, the terms "component," "system" and the like are intended to refer to a computer-related entity, either hardware, a combination of hardware and software, software, or software in execution. For example, a component may be, but is not limited to being, a process running on a processor, a processor, an object, an executable, a thread of execution, a program, and/or a computer. By way of illustration, both an application running on a computer and the computer can be a component. One or more components may reside within a process and/or thread of execution and a component may be localized on one computer and/or distributed between two or more computers or processors.

The word "exemplary" is used herein to mean serving as an example, instance, or illustration. Any aspect or design described herein as "exemplary" is not necessarily to be construed as preferred or advantageous over other aspects or designs.

Furthermore, the disclosed subject matter may be implemented as a system, method, apparatus, or article of manufacture using standard programming and/or engineering techniques to produce software, firmware, hardware, or any combination thereof to control a computer or processor-based device to implement aspects detailed herein. The term "article of manufacture" (or alternatively, "computer program product") as used herein is intended to encompass a computer program accessible from any computer-readable device, carrier, or media. For example, computer readable media can include but are not limited to magnetic storage devices (e.g., hard disk, floppy disk, magnetic strips), optical disks (e.g., compact disk (CD), digital versatile disk (DVD)), smart cards, and flash memory devices (e.g., card, stick). Additionally, it should be appreciated that a carrier wave can be employed to carry computer-readable electronic data such as those used in transmitting and receiving electronic mail or in accessing a network such as the Internet or a local area network (LAN). Of course, those skilled in the art will recognize that many modifications may be made to this configuration without departing from the scope or spirit of the claimed subject matter.

A 12-lead electrocardiogram (ECG) can include a I Lateral lead (also referred to as a I lead), a II Inferior lead (also referred to as a II lead), a III Inferior lead (also referred to as a III lead), an aVR lead, an aVL Lateral lead (also referred to as an aVL lead), an aVF Inferior lead (also referred to as an aVF lead), a V1 Septal lead (also referred to as a V1 lead), a V2 Septal lead (also referred to as a V2 lead), a V3 Anterior lead (also referred to as a V3 lead), a V4 Anterior lead (also referred to as a V4 lead), a V5 Lateral lead (also referred to as a V5 lead), and a V6 Lateral lead (also referred to as a V6 lead). These 12 different leads are produced from 10 electrodes attached to or otherwise in contact with a patient's body.

Although the present disclosure discusses data ingestion from a 12-lead ECG, it should be understood that it may be employed using data ingested from ECGs with more or fewer leads, provided the ECG used for training relies on a larger number of leads than the clinical or consumer device that is later used.

Similarly, although the portable or consumer devices to which the trained model is applied are generally referred to herein as having one lead, it should be understood that they may include a larger number of leads, provided that number is smaller than the number of leads on which the AI model is trained. For example, the device may be a single-lead device such as a smartwatch or other device worn on the wrist or a device worn around the chest. Alternatively, the device may be a multi-lead device such as a garment with a pair of embedded leads. Still further, the device may be a smaller, portable ECG device with, e.g., 1 to 6 leads, or it may even be a clinical grade device, e.g., with 12 leads. In the lattermost case, the device still preferably includes fewer leads than the device(s) from which the clinical data is obtained.

The present disclosure has applicability to multiple areas of medicine in which patient data is obtained via multi-lead ECGs. Such areas may include, but are not limited to, cardiology, oncology, endocrinology, and medical diagnostics. Such areas may benefit from the transfer learning method disclosed herein due to the variability that is introduced in data collection in each area. For example, in cardiology, oncology, and/or endocrinology, different machines will generate different reads, so the transfer learning method makes it possible to evaluate this disparate data from one machine to the next, particularly without having to batch normalize the data. Similarly, with regard to medical diagnostics, different labs may have their own procedures, biases, ranges for what is normal, etc. Additionally, data received from one patient or cohort of patients may need to be modified in order to render it applicable to a second cohort of patients, e.g., data from male patients and what is considered within normal ranges for them may need to be adjusted to apply it to female patients. Such modifications also may be accomplished through the transfer learning methods disclosed herein.

In some embodiments, the machine learning model may be applied to clinical data as part of a medical diagnostic. In this case, the clinical data can include outcome data, such as whether or not a patient developed a cardiac event or disease state such as AF in a time period following the day that the ECG was taken. In other embodiments, the clinical data may be used in a predictive sense, e.g., to determine based on that data a likelihood that the patient would develop a cardiac disease state such as AF, cardiac amyloidosis, or a different disease state within a certain time period following the day that the ECG was taken. In particular, the methods disclosed herein may be applied to a model such those disclosed in U.S. patent application Ser. Nos. 17/829,356 and 17/829,357, both filed May 31, 2022, and both titled "Artificial Intelligence Based Cardiac Event Predictor Systems and Methods, the contents of each which are incorporated by reference herein in their entirety.

The present disclosure employs a transfer learning method and/or an input translation method to train millions of AI model parameters to predict a patient's current or future health status with millions of 12-lead ECGs and paired clinical data from a healthcare provider. The method then includes taking the trained 12-lead model, extracting interpretation units for individual leads, and then reconstructing a model that will process data received from a clinical or consumer device that employs fewer leads. In one embodiment, the method then applies a fine-tuning step in which the reconstructed model learns to adapt to the new device's data, where that step requires just a couple hundred samples (as opposed to the original millions). In some embodiments, as further described below, the input translation method is applied to construct a 12-lead ECG signal from input data of a single-lead, and the generated 12-lead signal is provided to a risk model to assess a risk of the occurrence of a cardiac event. In other embodiments, AI models can transform 12-lead ECG data into single-lead ECG data, and the transformed data is then used to train a risk model.

Referring to FIG. 1, the method 100 may include one or more steps of data ingestion, quality assurance ("QA"), or preprocessing 102. Ingestion may include, e.g., a plurality of voltage-time traces where a first subset of traces is stored at a first frequency, e.g., 500 Hz, and a second subset of traces is stored at a second, different frequency, e.g., 250 Hz. Such data may be batch loaded due to the exceedingly large volume of clinical data being ingested, and similar batch techniques may be applied to one or both of the training or prediction steps disclosed herein.

In addition, QA in the method may include a time-series signal processing of ECG data including artifact detection and exclusion, while preprocessing may include time-series signal processing of ECG data. Artifacts may include those identified by ECG software at the time of ECG; for example, ECG outputs that include "technically limited", "motion/baseline artifact", "Warning: interpretation of this ECG, although attempted, may be adversely affected by data quality", "Acquisition hardware fault prevents reliable analysis", "Suggest repeat tracing", "chest leads probably not well placed", "electrical/somatic/power line interference", or "Defective ECG". QA also may include identifying and excluding one or more subsets of data. For example, when the model is designed to analyze individuals with respect to atrial fibrillation, a lead voltage over 12 mV may be considered an exclusion criterion and/or considered to usually occur as a result of motion artifacts. Thus, the method may perform a quality check in such instances and remove all ECG lead data at or above that threshold level. In another example, lead data reading 0 mV may be considered to result from a dead lead and may be deleted from the training set. Conversely, the method may retain such data for its model, recognizing that doing so may result in a dataset and model that are more robust. Other QA preprocessing steps may include sampling normalization, voltage trace structure changes, and possible inclusions of noisy data to regularize deep learning models. For example, dead leads and/or spikes in millivolts may be identified (such as over 12 mV).

The preprocessing at step 102 may include resampling the 250 Hz ECGs to 500 Hz, for example, by linear interpolation. Pre-processing also may be applied to data received from the portable or consumer device. For example, such devices may sample at different, lower frequencies than clinical ECGs, so such data also may be processed, e.g., by linear interpolation, to adjust for the difference.

At step 104, the deep neural network parameters may be pretrained on millions of 12-lead ECGs. This can involve just ECG data (unsupervised), or it may leverage associated clinical data wherein the ECG data for a given patient corresponds to known clinical conditions of the patient (supervised). In some embodiments, the clinical data can include outcome data, such as whether or not a patient developed a cardiac event such as atrial fibrillation ("AF") in a time period following the day that the ECG was taken.

The method also may include mid-training network modification. For example, the network may be pruned and a single channel featurization unit may be isolated. Such pruning may be useful to adapt the network to the specific portable or consumer device being used. For example, for wrist-worn devices, the system may determine that a model trained and isolated on readings taken from I lead or II lead may be most similar or most applicable. Alternatively, the system may determine that data derived from a different lead or combination of leads may be most applicable for a chest-worn device that is placed over the wearer's heart. Once such pruning is done, new neural layers then may be added to connect a single channel's features to a new classification layer. Additionally or alternatively, multiple channel featurization units may be isolated from the remaining units, and a combination of those units may be most similar to a single-lead signal from an ECG device. For example, the system may determine that a model trained on a combination of the I lead and the II lead may be most similar to the data from a single lead of a wrist-worn device.

Subsequently, at step 106, the method may resume training on a 12-channel ECG dataset to fine-tune the model, for example by using transfer learning plus additional layers to produce a model for the single-lead ECG devices. Upon completing the fine tuning, the method then may proceed at step 108 to apply and evaluate the model on data obtained from smaller-channel ECGs, such as 1-channel ECGs.

Figure 2:
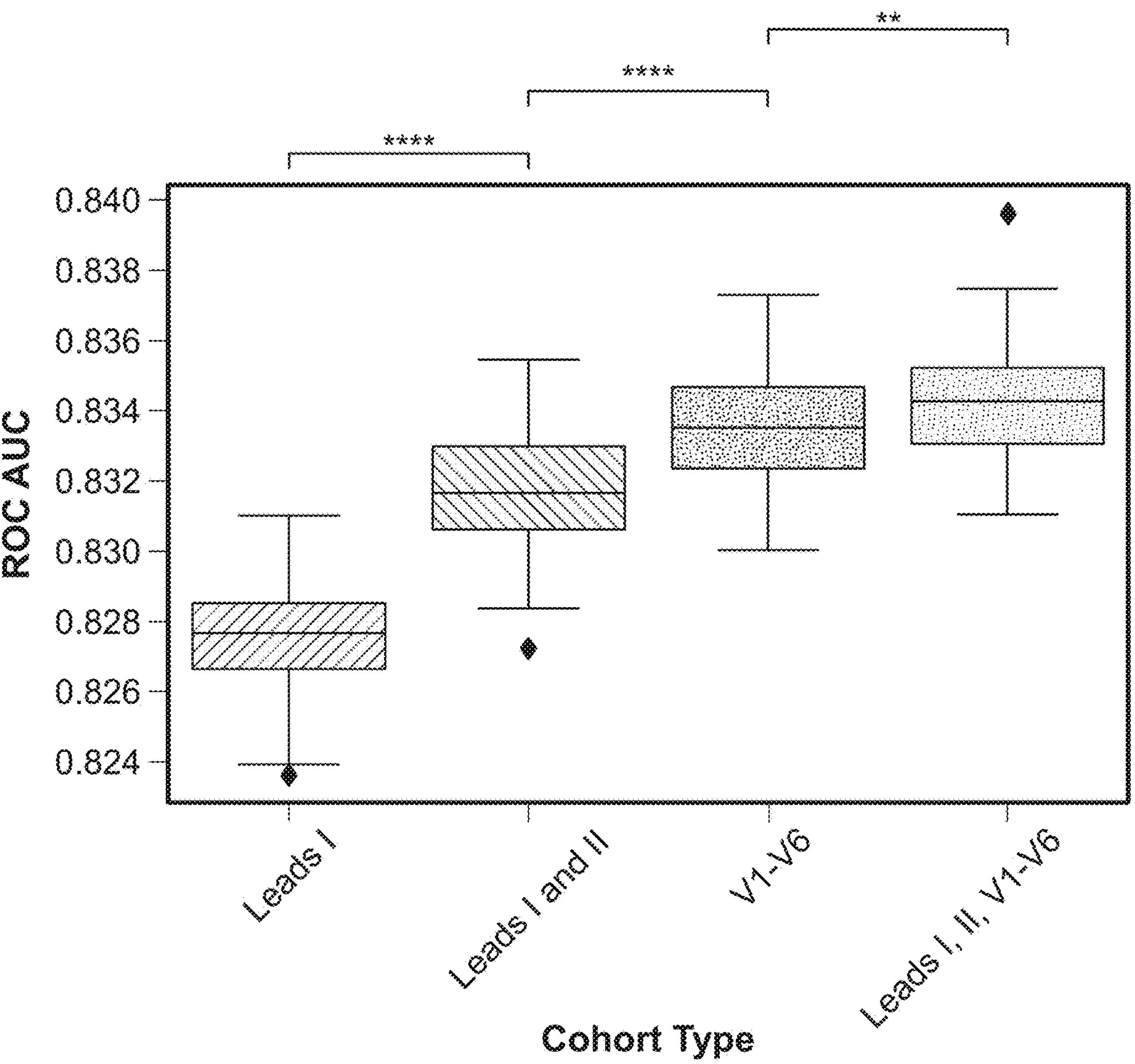
FIG. 2 is a bar chart of model performance as mean area under the receiver operating characteristic.
Figure 3:
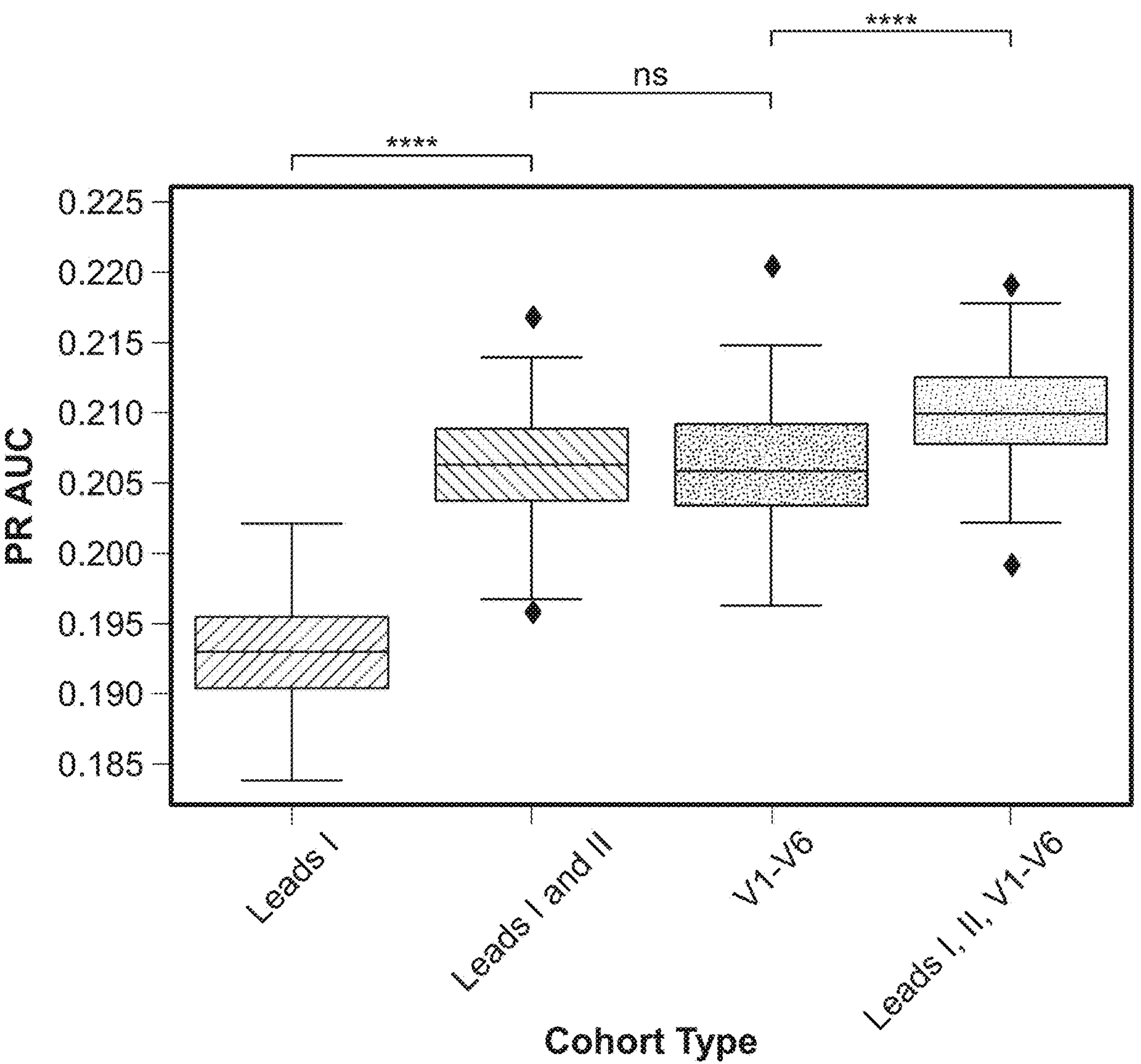
FIG. 3 is a bar chart of model performance as mean area under the precision-recall curve.

FIGS. 2 and 3 provide risk model performance metrics for 1 yr first time incident AF risk towards patients aged >=18 years. In both cases, Mann-Whitney U tests with Bonferroni corrections were used to assess significant differences between groups. "***" indicates statistically significant with a p-value <0.05, "ns" indicates that the difference between groups was not statistically significant, and "" indicates some statistical significance.

In particular, risk model performance in FIG. 2 is depicted using receiver operating characteristic area under the curve (ROC AUC). ROC AUC is a robust metric of model performance that represents the ability to discriminate between two classes. Higher ROC AUC suggests higher performance (with perfect discrimination represented by an ROC AUC of 1 and an AUROC of 0.5 being equivalent to a random guess).

Model performance in FIG. 3 is depicted using precision recall area under the curve (PR AUC). PR AUC is an average precision score determined by computing weighted average of precisions achieved at each threshold by the increase in recall.

The ROC AUC and PRC AUC of the model for the prediction of new onset AF within 1 year were approximately 0.828, 95% CI [0.827, 0.829] and 0.194 [0.192, 0.197], respectively, for Lead I, 0.832 [0.831, 0.833] and 0.207 [0.205, 0.209], respectively, for Leads I and II, 0.833 [0.0832, 0.835] and 0.207 [0.205, 0.210], respectively, for Leads V1-V6, and 0.834 [0.833, 0.836] and 0.210 [0.209, 0.211], respectively, for Leads I, II, and V1-V6.

These results demonstrate that the AI risk model may be properly trained on clinical data and then applied to data received from portable or consumer devices, permitting the use of cardiology analysis outside of a clinical setting.

Artificial intelligence models referenced herein may be gradient boosting models, random forest models, neural networks (NN), regression models, Naive Bayes models, or machine learning algorithms (MLA). NNs include conditional random fields, convolutional neural networks, attention based neural networks, deep learning, long short term memory networks, or other neural models. Additional exemplary models to be used within the method disclosed herein can be binary classification models, multiclass classification models, regression models, and the like. A single instance of the above models, or two or more such instances in combination, may constitute a model for the purposes of models, artificial intelligence, neural networks, or machine learning algorithms, herein.

A MLA or a NN may be trained from a training data set. In an exemplary prediction profile, a training data set may include ECG data from a large dataset of patients, which may also be supplemented with related clinical data, such as imaging, pathology, clinical, and/or molecular reports and details of a patient, such as those curated from an EHR or genetic sequencing reports. Training may include providing optimized datasets, labeling these traits as they occur in patient records, and training the MLA or NN to predict or classify based on new inputs.

In particular, the system may employ one or more neural networks to develop the cardio-related models discussed herein due, at least in part, to the flexibility of neural networks to handle ECG inputs. Artificial NNs are efficient computing models which have shown their strengths in solving hard problems in artificial intelligence. They have also been shown to be universal approximators (can represent a wide variety of functions when given appropriate parameters). The risk model may be implemented using a supervised NN. Supervised methods are useful when the training dataset has many known values or annotations, as may be the case when ECG data is used. Conversely, when the training dataset also includes clinical data such as data extracted or otherwise derived from EMR/EHR documents, the nature of those documents is that there may not be many annotations provided. In such cases, when exploring large amounts of unlabeled data, unsupervised methods may be useful for binning/bucketing instances in the data set. Unsupervised NNs may be employed, for example, where only positive samples are provided to the NN, which then may be trained to identify nuances with respect to those positive samples. When provided with negative samples, the NN then may recognize the absence of one or more of the nuances. Conversely, the NN may be trained on negative samples first and then, when applied to positive samples, it may be able to identify those samples as outliers.

As noted above, in cases where clinical data is associated with ECG data used to train the risk model (i.e., at least a portion of the data is labeled), the risk model can be a supervised learning model. In other embodiments, where the ECG data is unlabeled, unsupervised learning can be utilized to classify or assign risk ratings to results of the model.

Some of the models disclosed herein, for example, the transfer learning and/or input translation models discussed below for reconstructing 12 lead signal data from a 1 lead reading generated using a generative adversarial network (GAN) may be unsupervised. Conversely, the reverse operation effecting a 12 lead to 1 lead translation may be supervised as it uses the labels to train the model. That said, it should be understood that whether a supervised or unsupervised model is used is not dictated by the direction of the translation so that supervised or unsupervised models can be used in either direction. Additionally, whether the data is labeled or not may not be the sole factor in deciding whether the model being used is supervised or unsupervised, as a risk rating may be dependent on labels provided in paired data and may cluster results in an unsupervised fashion and output a score accordingly.

Figure 4A:
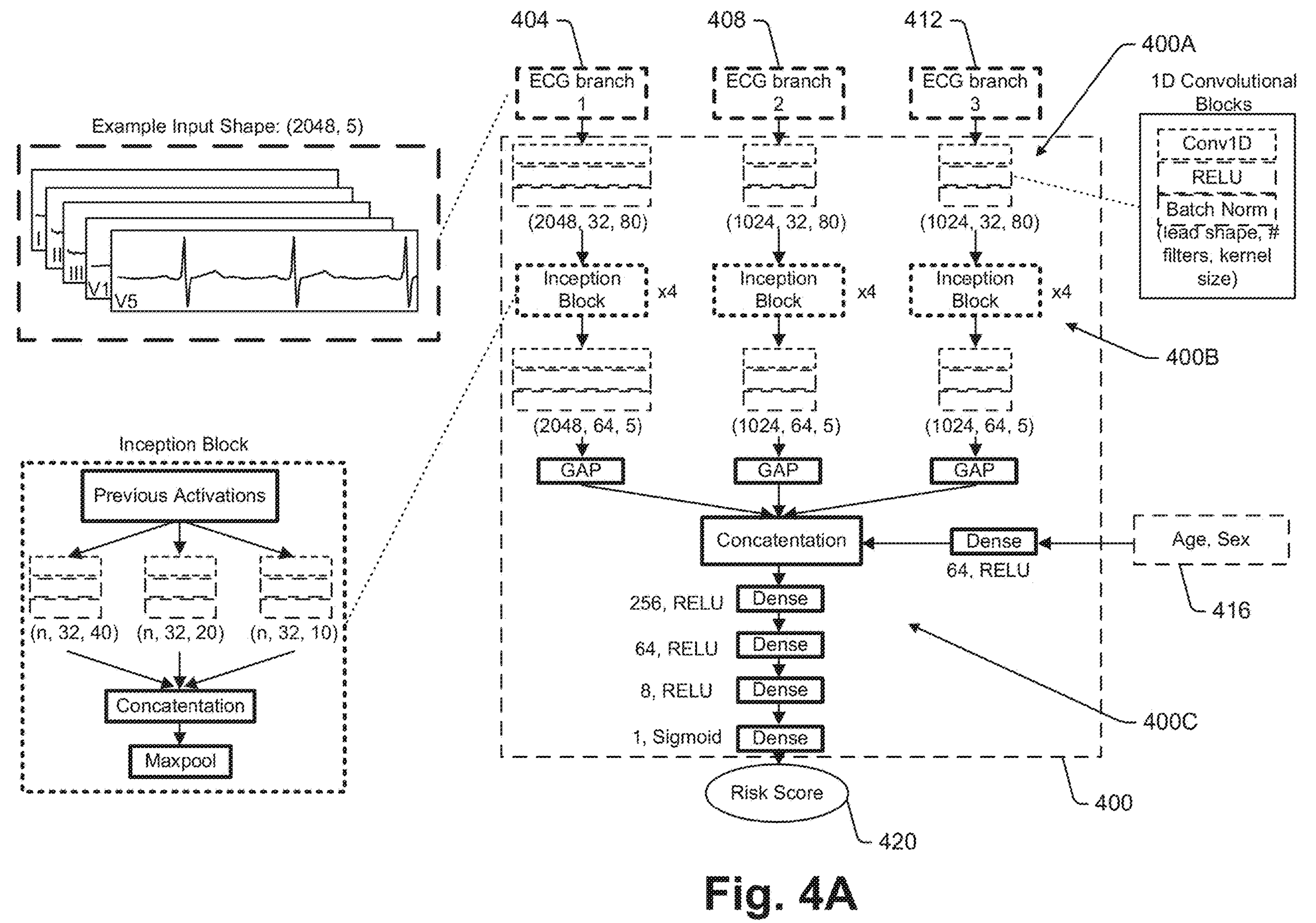
FIG. 4A is an exemplary embodiment of a model.

FIG. 4A is an exemplary embodiment of a risk model 400 usable with the transfer learning methods disclosed herein, for example, where the transfer learning methods utilize or are used to train one or more of the convolutional blocks 400A. Alternatively, the risk model 400 may be usable with the input translation methods disclosed herein, for example, by including those input translation methods in front of the risk model 400, so as to provide modified inputs to the risk model 400. Specifically, an architecture of the model 400 is shown. In some embodiments, the model 400 can be a deep neural network.

The input data structure to the model 400 can include a first branch 404 including leads I, II, V1, and V5, acquired from time (t)=0 (start of data acquisition) to t=5 seconds (e.g., the first voltage data, the sixth voltage data, the ninth voltage data, and the twelfth voltage data); a second branch 408 including leads V1, V2, V3, II, and V5 from t=5 to t=7.5 seconds (e.g., the second voltage data, the fourth voltage data, the seventh voltage data, the tenth voltage data, and the thirteenth voltage data); and a third branch 412 including leads V4, V5, V6, II, and V1 from t=7.5 to t=10 seconds (e.g., the third voltage data, the fifth voltage data, the eighth voltage data, the eleventh voltage data, and the fourteenth voltage data) as shown in FIG. 3. The arrangement of the branches can be designed to account for concurrent morphology changes throughout the standard clinical acquisition due to arrhythmias and/or premature beats. For example, the model 400 may need to synchronize which voltage information or data is acquired at the same point in time in order to understand the data. Because the ECG leads are not all acquired at the same time, the leads may be aligned to demonstrate to the neural network model which data was collected at the same time. It is noted that not every lead needs to have voltage data spanning the entire time interval. This is an advantage of the model 400, as some ECGs do not include data for all leads over the entire time interval. For example, the model 400 can include ten branches, and can be trained to generate a risk score based in response to receiving voltage data spanning subsequent one second periods from ten different leads. As another example, the model 400 can include four branches and can be trained to generate a risk score based in response to receiving voltage data spanning subsequent 2.5 second periods from four different leads. Certain organizations such as hospitals may use a standardized ECG configuration (e.g., voltage data spanning subsequent one second periods from ten different leads). The model 400 can include an appropriate number of branches and be trained to generate a risk score for the standardized ECG configuration. Thus, the model 400 can be tailored to whatever ECG configuration is used by a given organization.

In some embodiments, the model 400 can include a convolutional component 400A, inception blocks 400B, and a fully connected dense layer component 400C. The convolutional component 400A may start with an input for each branch followed by a convolutional block. Each convolutional block included in the convolutional component 400A can include a 1D convolutional layer, a rectified linear activation (RELU) activation function, and a batchnorm layer, in series. Next, this convolutional block can be followed by four inception blocks 400B in series, where each inception block 400B may include three 1D convolutional blocks concatenated across the channel axis with decreasing filter window sizes. Each of the four inception blocks 400B can be connected to a 1D maxpooling layer, where they are connected to another single 1D convolutional block and a final global averaging pool layer. The outputs for all three branches can be concatenated and fully connected to the dense layer component 400C. The dense layer component 400C can include four dense layers of 256, 64, 8 and 1 unit(s) with a sigmoid function as the final layer. All layers in the architecture can enforce kernel constraints and may not include bias terms. In some embodiments, the model 400 can be implemented using Keras with a TensorFlow backend in python and default training parameters were used except where specified. In some embodiments, AdaGrad optimizer can be used with a learning rate of 1 $e^{-4}$, a linear learning rate decay of 1/10 prior to early stopping for efficient model convergence at patience of three epochs, and batch size of 2048. In some embodiments, differing model frameworks, hypertuning parameters, and/or programming languages may be implemented. The patience for early stopping was set to 9 epochs. In some embodiments, the model 400 can be trained using NVIDIA DGX1 and DGX2 machines with eight and sixteen V100 GPUs and 32 GB of RAM per GPU, respectively.

In some embodiments, the model 400 can additionally receive electronic health record (EHR) data points such as demographic data 416, which can include age and sex/gender as input features to the network, where sex can be encoded into binary values for both male and female, and age can be cast as a continuous numerical value corresponding to the date of acquisition for each 12-lead resting state ECG. In some embodiments, other representations may be used, such as an age grouping 0-9 years, 10-19 years, 20-29 years, or other grouping sizes. In some embodiments, other demographic data such as race, smoking status, height, and/or weight may be included. In some embodiments, the EHR data points can include laboratory values, echo measurements, ICD codes, and/or care gaps. The EHR data points (e.g., demographic data, laboratory values, etc.) can be provided to the model 400 at a common location.

The EHR data points (e.g., age and sex) can be fed into a 64-unit hidden layer and concatenated with the other branches. In some instances, these EHR features can be extracted directly from the standard 12-lead ECG report. In some embodiments, the model 400 can generate ECG information based on voltage data from the first branch 404, the second branch 408, and the third branch 412. In some embodiments, the model 400 can generate demographic information based on the demographic data 416. In some embodiments, the demographic information can be generated by inputting age and sex into a 64-unit hidden layer. The demographic information can be concatenated with the ECG information, and the model 400 can generate a risk score 420 based on the demographic information and the ECG information. Concatenating the ECG information with the separately generated demographic information can allow the model 400 to individually disseminate the voltage data from the first branch 404, the second branch 408, and the third branch 412, as well as the demographic data 416, which may improve performance over other models that provide the voltage data and the demographic data 416 to the model at the same channel.

In some embodiments, the risk score 420 can be indicative of a likelihood the patient will suffer from a condition within a predetermined period of time from when electrocardiogram data (e.g., the voltage data from the leads) was generated. In some embodiments, the condition can be AF, mortality, ST-Elevation Myocardial Infarction (STEMI), Acute coronary syndrome (ACS), stroke, or other conditions indicated herein. In some embodiments, the model 400 can be trained to predict the risk of a patient developing AF in a predetermined time period following the acquisition of an ECG based on the ECG. In some embodiments, the time period can range from one day to thirty years. For example, the time period may be one day, three months, six months, one year, five years, ten years, and/or thirty years. In some embodiments, the predicted risk can be a binary classification classifying the patient as either at risk or not at risk, rather than providing a numerical score.

Figure 4B:
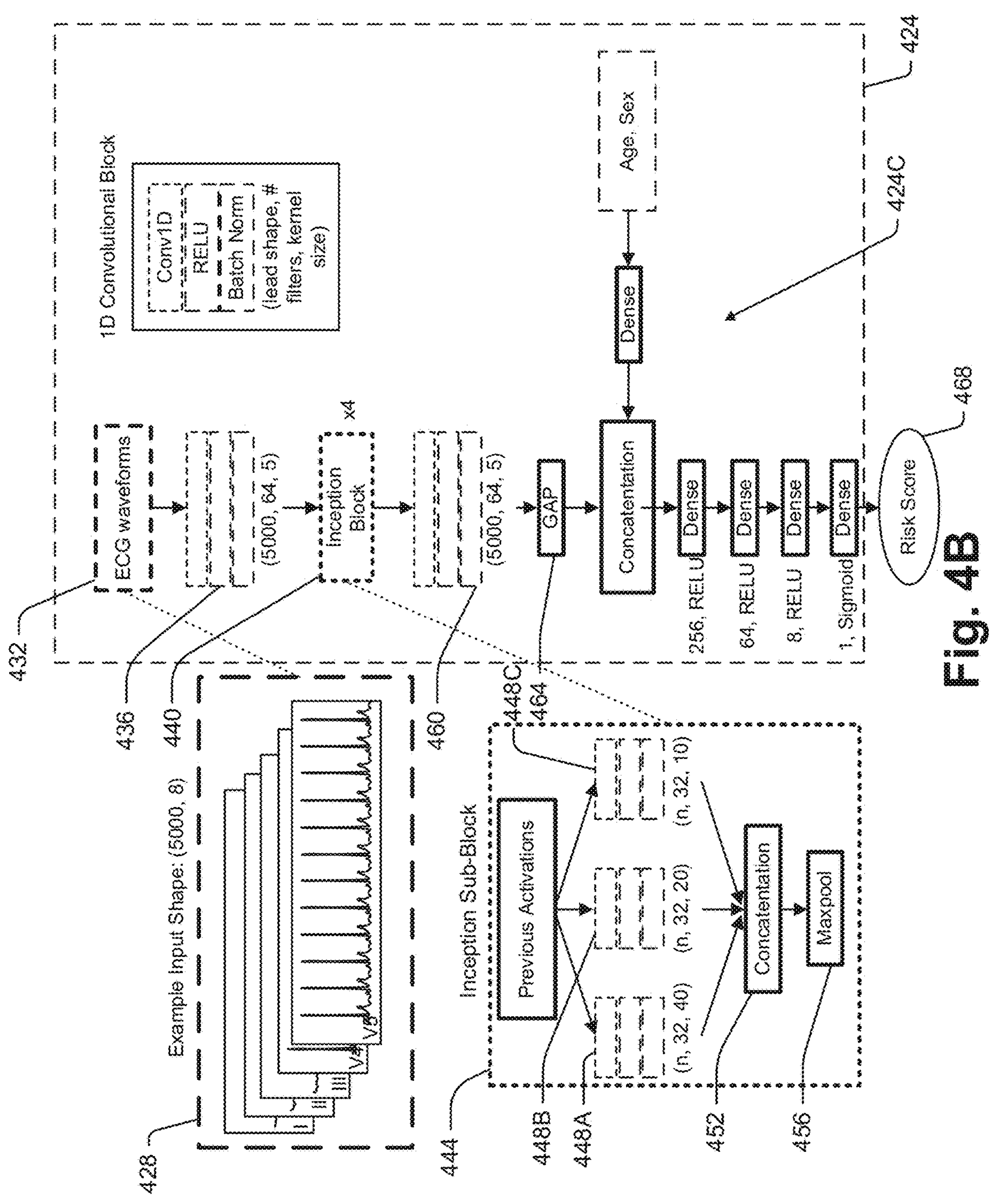
FIG. 4B is another exemplary embodiment of a model.

FIG. 4B is another exemplary embodiment of a risk model 424 usable with the input translation methods or the transfer learning methods disclosed herein, similar to the manner in which those methods are used in connection with the risk model of FIG. 4A. Specifically, another architecture of the model 400 in FIG. 4A is shown. In some embodiments, the model 424 in FIG. 4B can receive ECG voltage data generated over a single time interval.

In some embodiments, the model 424 can be a deep neural network. In some embodiments, such as is shown in FIG. 4B, the model 424 can include a single branch 432 that can receive ECG voltage input data 428 generated over a single time interval (e.g., ten seconds). As shown, the model 424 can receive ECG voltage input data 428 generated over a time interval of ten seconds using eight leads. In some embodiments, the ECG voltage input data 428 can include five thousand data points collected over a period of 10 seconds and 8 leads including leads I, II, V1, V2, V3, V4, V5, and V6. Alternatively, as discussed above, the ECG voltage input data 428 can be collected from 12 leads as in a standard 12-lead ECG or from some other plurality of leads. The number of data points can vary based on the sampling rate used to sample the leads (e.g., a sampling rate of five hundred Hz will result in five thousand data points over a time period of ten seconds). The ECG voltage input data 428 can be transformed into ECG waveforms.

As described above, in some embodiments such as where the ECG voltage input data is collected from 8 leads, the ECG voltage input data 428 can be "complete" and contain voltage data from each lead (e.g., lead I, lead V2, lead V4, lead V3, lead V6, lead II, lead VI, and lead V5) generated over the entire time interval. Thus, in some embodiments, the predetermined ECG configuration can include lead I, lead V2, lead V4, lead V3, lead V6, lead II, lead VI, and lead V5 having time intervals of 0-10 seconds. The model 424 can be trained using training data having the predetermined ECG configuration including lead I, lead V2, lead V4, lead V3, lead V6, lead II, lead VI, and lead V5 having time intervals of 0-10 seconds in the case of an 8-lead ECG. When all leads share the same time intervals, the model can receive the ECG voltage input data 428 at a single input branch 432. Otherwise, the model can include a branch for each unique time interval as described above in conjunction with FIG. 4A.

The ECG waveform data for each ECG lead may be provided to a 1D convolutional block 436, which can also be referred to as a convolutional layer, where the layer definition parameters (n, f, s) refer, respectively, to the number of data points input presented to the block, the number of filters used, and the filter size/window. In some embodiments, the number of data points input presented to the block can be five thousand, the number of filters used can be thirty-two, and the filter size/window can be eighty. The 1D convolutional block 436 can generate and output a downsampled version of the inputted ECG waveform data to the inception block. In some embodiments, the first 1D convolutional block 436 can have a stride value of two.

The model 424 can include an inception block 440. In some embodiments, the inception block 440 can include a number of sub-blocks. Each sub-block 444 can include a number of convolutional blocks. For example, each sub-block 444 can include a first convolutional block 448A, a second convolutional block 448B, and a third convolutional block 448C. In the example shown in FIG. 4B, the inception block 440 can include four sub-blocks in series, such that the output of each sub-block is the input to the next sub-block. Each inception sub-block can generate and output a downsampled set of time-series information. Each sub-block can be configured with filters and filter windows as shown in the inception block 440 with associated layer definition parameters.

In some embodiments, the first convolutional block 448A, the second convolutional block 448B, and the third convolutional block 448C can be 1D convolutional blocks. Results from each of the convolutional blocks 448A-C can be concatenated 452 by combining the results (e.g., arrays), and inputting the concatenated results to a MaxPool layer 456 included in the sub-block 444. The MaxPool layer 456 can extract positive values for each moving 1D convolutional filter window, which allows for another form of regularization and model generalization, and prevents overfitting. After completion of all four inception block processes, the output is passed to a final convolutional block 460 and then a global average pooling (GAP) layer 464. The purpose of the GAP layer 464 is to average the final downsampled ECG features from all eight independent ECG leads into a single downsampled array. The output of the GAP layer 464 can be passed into the series of dense layer components 424C as in conjunction with FIG. 4A (e.g., at the dense layer component 400C). Furthermore, optimization parameters can also be set for all layers. For example, all layer parameters can enforce a kernel constraint parameter (max_norm=3), to prevent overfitting the model. The first convolutional block 436 and the final convolutional block 460 can utilize a stride parameter of n=1, whereas each inception block 440 can utilize a stride parameter of n=2. The stride parameters determine the movement of every convolutional layer across the ECG time series and can have an impact on model performance. In some embodiments, the model 424 can also concatenate supplementary data such as age and sex as described above in conjunction with FIG. 4A, and the model 424 can utilize the same dense layer component architecture as the model 400. The model 424 can output a risk score 468 based on the demographic information and the ECG information. Specifically, the dense layer components 424C can output the risk score 468. In some embodiments, the risk score 420 can be indicative of a likelihood the patient will suffer from a condition within a predetermined period of time from when electrocardiogram data (e.g., the voltage data from the leads) was generated. In some embodiments, the condition can be AF, mortality, ST-Elevation Myocardial Infarction (STEMI), Acute coronary syndrome (ACS), stroke, or other conditions indicated herein. In some embodiments, the model 400 can be trained to predict the risk of a patient developing AF in a predetermined time period following the acquisition of an ECG based on the ECG. In some embodiments, the time period can range from one day to thirty years. For example, the time period may be one day, three months, six months, one year, five years, ten years, and/or thirty years.

In one embodiment, the convolutional neural networks, such as those depicted in FIGS. 4A and 4B, may be trained on a first set of data and translated to perform on a second set of data. In one example, the first set of data may be robust and include large quantities of samples from which to train while the second set of data may be sparse and include only a few quantities of samples. While the disclosure herein generally focuses on the first set of data being ECG data, it will be understood that the methods disclosed herein may be applicable to other types of data instead of or in addition to ECG data. For example, the first set of data may include more operational parameters or features, such as having access to more clinical data or more complete diagnostic data. Diagnostic data may include those from different disease states such as oncology, cardiology, endocrinology, and diagnostic laboratory testing. In the field of oncology, for example, a first dataset may include the full RNA transcriptome and subsequent read quantities generated from next generation sequencing while the second set of data may have been generated from a greatly reduced number of transcriptomes such as those generated from a smaller panel or microarray. In the field of endocrinology and diagnostic laboratory testing, for example, a first dataset may include the diagnostics such as blood glucose test, glycosylated hemoglobin test (A1c), thyroid stimulating hormone test (THS), luteinizing hormone test (LH), follicle stimulating hormone test (FSH), total testosterone test, thyroglobulin test (Tg), or other blood tests to detect levels of hormones, such as cortisol, 17 hydroxyprogesterone, DHEA-sulfate, ACTH, aldosterone, vitamin D, PTH, prolactin and various forms of estrogen. Tests performed on laboratory equipment may have significantly greater accuracy than a second dataset which may include tests performed via smaller, portable equipment such as a glucometer, or exhibit biases when compared to readings of the same patient's blood performed on the laboratory equipment from another location.

In another example, a model may be translated from training from one sequencing laboratory to another sequencing laboratory due to the differences in the laboratory's equipment or sequencing procedures. In such an example, the datasets may not be categorized as robust to sparse but instead as robust to robust, including where there exists disparity between the data. One aspect of translating a model trained on a robust dataset to another robust dataset is that the model maintains performance while becoming generalizable across many different robust datasets without concern for where they were generated.

Multiple embodiments may be implemented on data varying in quantity, quality, and number of features. In general, a model may be trained on a dataset having high quantity of samples, higher quality of samples, and/or higher number of features for each sample, and may be translated to a dataset having a lower quantity of samples, lower quality of samples, and/or a lower number of features for each sample. In this manner, higher quality predictive algorithms may be adapted for performance on datasets having one or more disadvantages that preclude the dataset from being used to generate a higher quality model.

Similar to RNA as presented above, a model trained on a first DNA panel may be translated using a second DNA panel in either a robust to sparse translation or a robust to robust translation.

If a user attempted to input the reduced data set into a model trained from the robust dataset, the results generated would not be accurate due to the differences in data. However, if the model was translated from the first dataset to the second dataset, much of the performance of the model generated from the robust training set of data may be retained for use with the reduced set of data.

In the field of endocrinology, a similar translation may be performed, for example, on sequencing data generated for treating a patient having diabetes, or other endocrinological diagnosis.

In the field of mental health, a similar translation may be performed, for example, on sequencing data generated for treating a patient having depression, or other mental health diagnosis.

In the field of laboratory testing, a similar translation may be performed, for example, on diagnostic laboratory tests for metabolic panels, blood panels, viral or bacterial panels, or other laboratory diagnostic testing.

Steps for translating the model may include performing one or more transfer learning methodologies.

In the field of cardiology, the robust dataset may include 12 lead ECGs across millions of patients while the reduced dataset may be limited to a few leads such as those generated from one or more wearable devices. In some embodiments, the translation may be performed across different ECG collection devices, whether having the same number of leads in a robust to robust translation, a differing number of leads in a robust to robust translation, a same number of leads in a robust to sparse translation, or a differing number of leads in a robust to sparse translation. As used herein, robust may refer to the number of samples in the dataset, the quality of samples in the dataset, or the number of features associated with the samples of the dataset.

The deep neural network parameters may be pretrained on millions of 12-lead ECGs. This can involve just ECG data (unsupervised), or it may leverage associated clinical data such as patient demographics, diagnoses, or cardiac anatomy and functional measures (blood flow from heart) (supervised). In some embodiments, the clinical data can include outcome data, such as whether or not a patient developed AF or another cardiac disease state in a time period following the day that the ECG was taken. The resulting neural network may be composed of model-specific convolutional layer blocks, and/or fully connected layers, such as those presented in exemplary architectures 4A and 4B.

The method also may include mid-training network modification. For example, the network may be pruned and a single channel featurization unit may be isolated as the model is being trained. The single channel featurization unit to be isolated can be the channel featurization unit that includes input data from a lead that most closely resembles the single lead input of a portable device or the single lead sought to be used for data collection to which the trained model is applied. In some cases, similarity between the single lead input and the single channel featurization unit can be determined experimentally by first formatting the input data of a single-lead to be comparable to the data from the featurization channels from the 12-lead ECG, then testing the performance for the outcome of interest, comparing to the single channels of the 12-lead ECG. This process may be repeated for one or more others of the plurality of leads, with the results compared in order to determine the best-performing channel featurization unit. Such pruning may be useful to adapt the network to the specific portable or consumer device being used. For example, for wrist-worn devices, the system may determine that a model trained and isolated on readings taken from I lead or II lead may be most similar or most applicable. Alternatively, the system may determine that data derived from a different lead or combination of leads may be most applicable for a chest-worn device that is placed over the wearer's heart. By identifying a corresponding lead within the trained convolutional network, it may be held out from pruning or selected for pruning based on the desire to include or exclude it from the translated model. Once such pruning is done, new neural layers may then be added to connect a single channel's features to a new classification layer.

The system may determine which features of the neural network are to be pruned by first identifying the most important features. Importance may be determined by bypassing neurons in the network and scaling the nodes' importance via measuring the performance degradation of the output of the network, filtering out neurons which fall below a threshold for their weights, or otherwise filtering out unnecessary neurons using other pruning methods. In some embodiments, methods used in pruning a network can include Oracle pruning or ranking, or Taylor criteria ranking.

The process of transfer learning and fine-tuning may include leveraging learnings obtained in training of a similar model. For example, a model obtained through training on a 12-node ECG can include multiple convolutional layers, each layer performing a transformation on the data input into the layer to produce output data from the layer. Models for use with single-node ECGs that are similar but not identical to the 12-node ECGs can be trained using insights or learnings from the models trained on the 12-node ECGs. In particular, training models for single node ECG devices can preserve layers of the trained 12-node ECG model, while adding convolutional layers for further processing of the data for single-node ECGs. Preserving layers of a similar model, as previously described, can sometimes be referred to as "freezing" the layer, as training the similar model does not involve any training or modification of the data values in the frozen layers. Thus, the inputs for the single-node ECG data may undergo the same initial sequence of transforms or convolutions as the data 12-node, and can further undergo additional transforms by being processed through the additional convolutional layers for the 1-node ECG. In one aspect, the additional layers can be trained using generational adversarial networks, as further described below. Once the new layer(s) have been trained, the method then may include a fine-tuning step, in which some or all of the entire model is unfrozen and then retrained on the new data used to train the additional layer(s). In this case, however, a low learning rate as part of this retraining so as to avoid overfitting of the model.

In one embodiment, the frozen layers may be the GAP layers of FIGS. 4A and 4B. In another embodiment, the frozen layers may be the dense layers of FIGS. 4A and 4B. In yet another embodiment, one or more of the GAP layers may be selected for freezing and or other layers as identified using the rule set or heuristic algorithms. Preferably, the layers selected for freezing are earlier or upstream in the neural network relative to the layers being trained.

In another example, pruning the network and extracting a subset (1 to 12) of the lead featurization units may be performed via a derived insights table with pre-programmed rules, or in a programmatic manner using one or more optimization or heuristic models before adding new neural layers to connect channel features to a new classification layer.

Subsequently the translation steps may resume training on a 1-channel ECG dataset to fine-tune the model before being able to apply and evaluate the transformed model on data obtained from smaller-channel ECGs, e.g., 1-channel ECGs. Fine-tuning may include training on a dataset that matches the pruned input structure. Fine-tuning strategies can either freeze the extracted ECG layers and retrain the unfrozen final layers, or "un-freeze" the ECG layers to further modify the featurization of ECG leads. Modifying which layers are exempt from retraining at each fine-tuning iteration enables the model to select for the best layers to reweigh and improve the resulting translated model. For example, in some embodiments, fine-tuning can involve iterating through models trained on 12-lead ECG data to obtain a model that produces the best classification for single lead ECG data. The model can first be trained as described above using frozen layers of a model trained with 12-lead ECG data, and, in some cases, paired data (e.g., clinical data, demographic data, etc.). Additional models for single-lead ECG inputs can further be generated using the learning from this model, and trained on the input data from individual channels (e.g., data from a single lead is input into the model, and additional layers are added to the layers of the model trained with the 12-lead ECG inputs). In some cases, this is performed for each individual channel, until a model has been obtained for each channel or lead, using frozen layers from the model trained with the 12-nodes and paired data. In some embodiments, the resultant model is fine-tuned at a lower learning rate (e.g., 1 order of magnitude less) to keep the information learned from the 12-lead model. The individual single-channel model that most closely resembles an input from a single-lead ECG device can be used for data obtained from the single lead ECG device to generate a risk rating given a single lead input.

In one embodiment, the frozen layers may be the GAP layers of FIGS. 4A and 4B. In another embodiment, the frozen layers may be the dense layers of FIGS. 4A and 4B. In yet another embodiment, one or more of the GAP layers may be selected for freezing and/or other layers as identified using the rule set or heuristic algorithms. In some embodiments, a process or algorithm for determining which layers to freeze can involve first freezing all but the final layer (e.g., the predictive layer). The model can iteratively be fine-tuned to determine the optimal selection and number of layers to freeze. In each iteration, the layer immediately upstream or before the last unfrozen layer can be unfrozen, and the resulting model is evaluated against the paired data to determine whether there is a boost or degradation to learning transference. Fine-tuning can thus identify the layers to be frozen by identifying the layer at which unfreezing ceases to provide a benefit to transfer learning, or where unfreezing in fact degrades the model's performance.

In some embodiments, the method may be diagnostic, whereby the clinical data can include outcome data, such as whether or not a patient developed AF in a time period following the day that the ECG was taken. In other embodiments, the clinical data may be used in a predictive sense, e.g., to determine based on that data a likelihood that the patient would develop AF within a certain time period following the day that the ECG was taken. In still other embodiments, the method may be used to predict multiple leads from a single or fewer leads at high enough accuracy to maintain performance on a pre-trained 12-lead model used for other evaluative purposes, such as predicting an occurrence within a certain time period following the day the ECG was taken of an echocardiogram-confirmable disease, such as in U.S. patent application Ser. No. 17/829,351, filed May 31, 2022, the contents of which are incorporated by reference herein in their entirety.

When considering one or more models within a collection of models, there is an advantage to identifying models susceptible to transfer learning. That is, models which have a strong signal attributable to a fewer number of leads than which the model is trained with may be preferred. A signal filtering service, such as identifying which process for identification of signals susceptible to transfer learning may include experimentally pruning channels from training inputs, or freezing or unfreezing layers of a CNN to identify channels of the training data either producing the strongest signal, or most closely approximating the signal of a single-lead ECG device.

Susceptible models may then be compared to available wearable devices, such that a wearable device may be identified that approximates the signal and a compatible pairing has been found. Pairs may be recorded for future translations or they may be automatically translated according to the methods disclosed herein. A compatibility service, such as linking wearable devices to transferable signals may include performing a lookup to data provided in a database containing the recorded pairs, or could alternatively include monitoring data obtained from the single-lead device and comparing to known testing data to identify the appropriate model based on the similarities of the single-lead to a lead or combination of leads of a 12-lead device, and applying a corresponding transfer learning model to data obtained from the single lead device, according to the methods described above.

In some cases, translational models trained on 12-lead ECG data can be used, alternatively or in addition to transfer learning models, to produce models for use with single-lead ECG devices, or devices with fewer than 12 leads. For example, an adapter can be trained to translate the 12-lead ECG training data to single-lead ECG data, and a risk model can be trained with the resultant single-lead ECG data. The risk model developed in this embodiment can then be applied to single-lead ECG production data to produce a risk rating therefor. In another embodiment, an adapter can be trained to produce 12-lead ECG data from a single lead. The 12-lead ECG data produced by the model can then be input into a risk model trained on 12-lead ECG data to produce a risk rating. Thus, in this embodiment, production single-lead ECG data can be provided to a translational model (e.g., an adapter) for conversion to 12-lead ECG data, and the output can be provided to the risk model to produce a risk rating based on the 12-lead input. According to these embodiments, data must first be adapted through transforming the data into the appropriate domain, whether transforming a single-lead ECG input into a 12-lead ECG input for use with a trained risk rating model, or generating a risk rating model for single lead inputs by first transforming labeled 12-lead training inputs into single lead format, and generating a risk rating model from the resultant data. For example, in some embodiments, a generative adversarial network ("GAN") can be used to produce a model for predicting 8 or 12 lead input data from input data of a single lead, where the single lead data is similar to the data that would be obtained in a production setting. This reconstruction can be useful where a risk model has been pre-trained using 12-node ECG data, and thus, given input data from a 12-lead ECG reading, or a 12-lead reconstruction from a single lead reading, risk can be assessed (i.e., probable incidence of AF). To produce the model, a generative adversarial network comprising a generator and a discriminator can be used. The generator is a model that, given input data of a single lead of a 12-lead ECG, generates predictions for input data of the remaining leads. The discriminator is a model that distinguishes or discriminates between production data (i.e., real 12-lead input data obtained in a production setting), and data produced using the generator model. The generator model can be sufficiently trained when the discriminator model is unable to reliably distinguish between production data and data produced by the generator model. Thus, according to some aspects, a risk rating can be determined from data of single-lead ECG devices by using a generative model to construct 12-lead data from input data of a single lead ECG device, and using the constructed 12-lead data as input into pre-trained 12-lead model for assessing risk.

Figure 5:
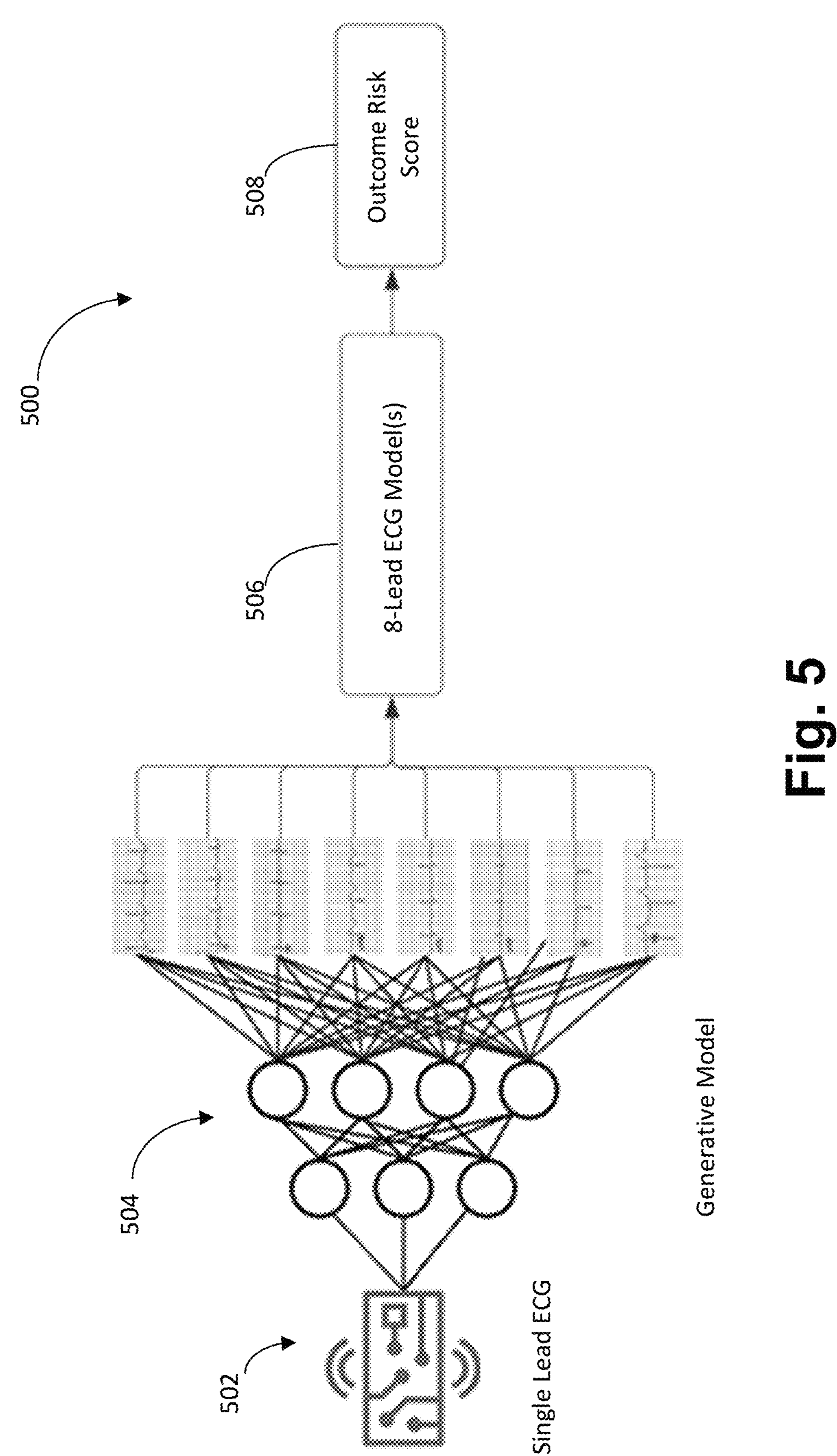
FIG. 5 is a diagram exemplifying one use case of the present disclosure.

As exemplified by the diagram 500 of FIG. 5, the disclosure herein relates to a first use case involving an n-lead to 12-lead reconstruction, where n leads are received at 502 and where n is 1 or some number smaller than 12. The n leads then are provided as inputs to a trained model 504, such as a generative model, where the model has been trained on data from a larger number of leads, such as a traditional 12-lead ECG or an 8-lead ECG. The model then may be used as part of that reconstruction to predict m-leads as at 506, where m is some number larger than n, such as 8 or 12, with the results of that prediction being comparable to those derived from an m-lead input. The prediction then may be used, for example, to generate a risk score as at 508, where the risk score may be indicative of a patient experiencing a cardiac disease state such as atrial fibrillation, aortic stenosis, cardiac amyloidosis, a disease state confirmable by echocardiography, and/or some other cardiac disease state within a certain time following capture of the p-lead data.

Figure 6:
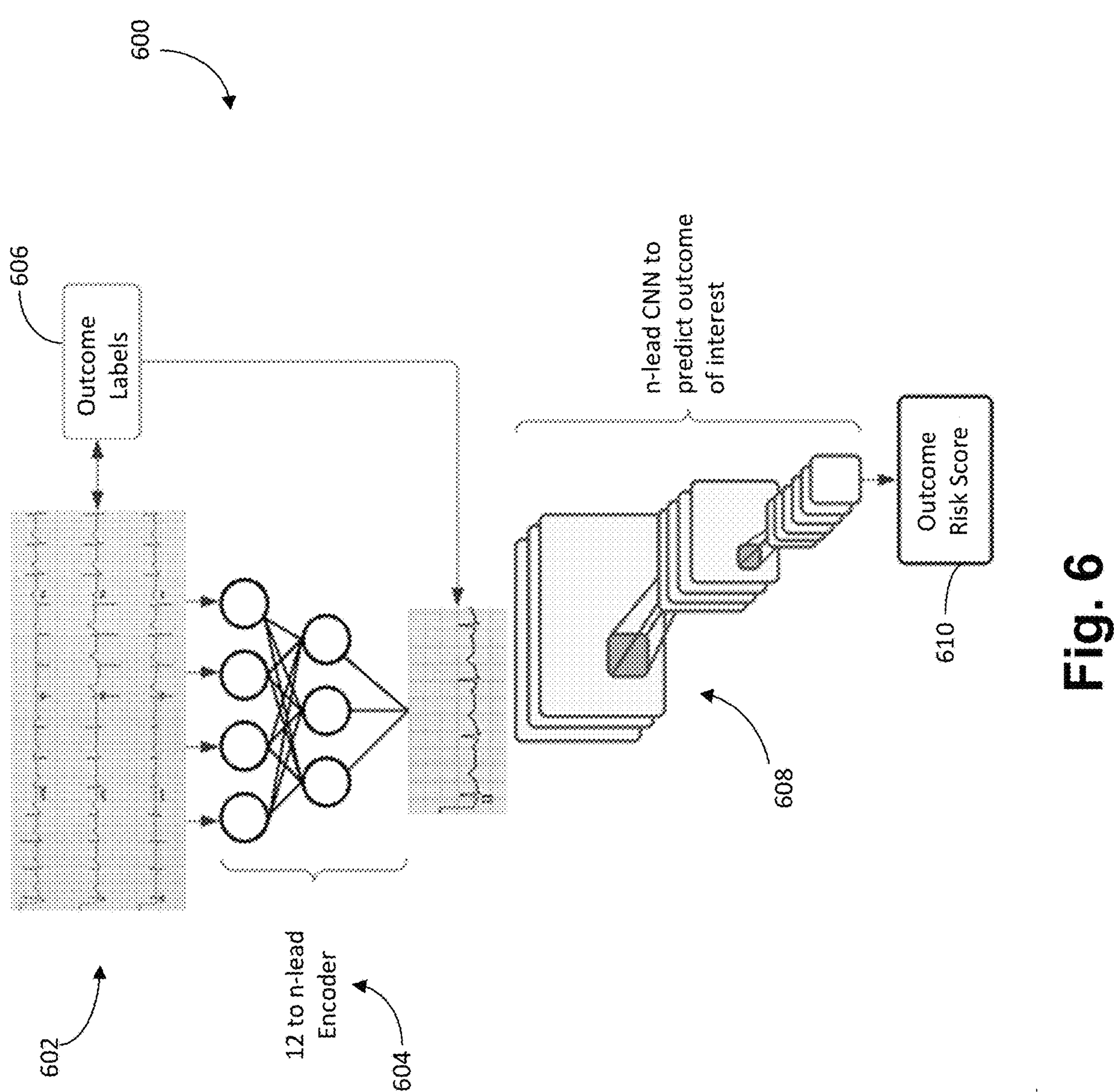
FIG. 6 is a diagram exemplifying a second use case of the present disclosure.

In another aspect, as exemplified by the diagram 600 of FIG. 6, the disclosure herein may relate to a second use case involving a 12-lead to n-lead reconstruction, where n again is 1 or some number smaller than 12. In this aspect, a single lead or a few leads of 12-lead ECG data may not be similar to the data obtained from a single lead or n-lead, such as the data received from a wearable device that obtains n-lead data, due, for example, to a data distribution shift. In this case, 12-lead data may be received as at 602 and delivered to a 12-to-n-lead encoder 604. The encoder may have been trained using other 12-lead data to project 12-lead data into a production n-lead ECG space using paired ECG data. Once trained, the encoder 604 then may be used, along with outcome labels 606, to transform the 12-lead data into an n-lead ECG space. That n-lead transformed data then may be used at 608 using a convolutional neural network or other machine learning model to predict an outcome of interest, which may be represented as an outcome risk score 610.

In other embodiments, it can be useful to produce a disease prediction model by first producing a model to translate or encode 12-lead ECG data to n-lead data, where n is a number of leads less than 12 (e.g., 1). The encoder model can be trained using 12-lead ECG and paired data, where the paired data can include clinical data or demographic data of a patient associated with the ECG data. The model can be trained to encode the 12-lead ECG data into a single-lead format. The models can be generated using training and learning transfer techniques described above. In some embodiments, the training data is labeled, including clinical information related to the 12-lead ECG training data. Thus, training the model can further include training a disease prediction model, which can use the labeled n-lead outputs of the encoder model. Once trained, the disease prediction model can be applied to produce a risk score given single-lead ECG inputs. The risk score can be a binary risk score, a multi-label risk score, or a regression score. This method can be particularly useful in some contexts, including where paired data is available for single lead ECG production data inputs. Further, this method may be advantageous where available training data includes paired single-lead ECG data and paired 12-lead ECG data, such that the encoder model can use supervised learning to produce the model, as compared with unsupervised learning models such as those produced with GAN methods.

While the invention may be susceptible to various modifications and alternative forms, specific embodiments have been shown by way of example in the drawings and have been described in detail herein. However, it should be understood that the invention is not intended to be limited to the particular forms disclosed.

Thus, the invention is to cover all modifications, equivalents, and alternatives falling within the spirit and scope of the invention as defined by the following appended claims.

What is claimed is:

1. A system comprising:

at least one memory; and at least one processor coupled to the at least one memory, the system configured to cause the at least one processor to execute instructions stored in the at least one memory to:

receive first electrocardiogram (ECG) data associated with a plurality of subjects and an electrocardiogram configuration including a predetermined set of leads and a time interval, the predetermined set of leads defining a first number and configuration of leads, the first electrocardiogram data comprising, for each lead included in the predetermined set of leads, voltage data associated with at least a portion of the time interval, identify a first artificial intelligence model for a particular cardiac disease state;

train the first artificial intelligence model on the first ECG data;

receive second ECG data derived from a particular device, the second ECG data being associated with a second number of leads, the second number of leads being fewer leads than the first number of leads;

select, from the predetermined set of leads, a training lead or combination of leads that most closely resembles the at least one lead of the particular device, at least in part by iteratively replacing data from one or more leads of the predetermined set of leads with ECG data associated with the second number of leads and evaluating performance of each iteration of the first artificial intelligence model;

fine-tune the first artificial intelligence model by iteratively identifying one or more frozen layers and one or more unfrozen layers, freezing the one or more frozen layers, and retraining the unfrozen layers, wherein subsequent iterations comprise unfreezing upstream layers from a last frozen layer;

train a second artificial intelligence model using a training dataset comprising ECG data including the predetermined set of leads, the second artificial intelligence model being configured to generate artificial ECG data corresponding to each lead of the predetermined set of leads based on the training lead or combination of leads;

input the second ECG data into the trained second artificial intelligence model;

translate, by the second artificial intelligence model, the second ECG data into artificial ECG data corresponding to each of the leads of the predetermined set of leads; and process, by the first artificial intelligence model, the artificial ECG data to generate one or more predictions regarding the particular cardiac disease state.

2. The system of claim 1, wherein the second artificial intelligence model is trained using a generative adversarial network.

3. The system of claim 1, wherein the one or more predictions include a likelihood of experiencing a cardiac disease state within a predetermined period of time from when the particular device generates the second ECG data.

4. The system of claim 1, wherein the system further is configured to cause the at least one processor to execute instructions stored in the at least one memory to:

display a notification relating to the one or more predictions on a display screen of the particular device.

5. The system of claim 4, wherein the particular device includes a wearable device, and wherein the wearable device is wearable on a wrist or around a chest of a user.

6. The system of claim 1, wherein the second number of leads is one lead.

7. The system of claim 1, wherein the predetermined set of leads comprises 12 leads.

8. A computer program product, the computer program product comprising instructions stored on a non-transitory computer readable medium to cause at least one processor on a computer to:

receive first electrocardiogram (ECG) data associated with a plurality of subjects and an electrocardiogram configuration including a predetermined set of leads and a time interval, the predetermined set of leads including a first number of leads, the first electrocardiogram data comprising, for each lead included in the predetermined set of leads, voltage data associated with at least a portion of the time interval, identify a first artificial intelligence model for a particular cardiac disease state;

train the first artificial intelligence model on the first ECG data;

receive second ECG data derived from a particular device, the second ECG data being associated with a second number of leads, the second number of leads being fewer leads than the first number;

select, from the predetermined set of leads, a training lead that most closely resembles at least one lead of the particular device, at least in part by iteratively replacing data from one or more leads of the predetermined set of leads with ECG data associated with the second number of leads and evaluating performance of each iteration of the first artificial intelligence model;

fine-tune the first artificial intelligence model by iteratively identifying one or more frozen layers and one or more unfrozen layers, freezing the one or more frozen layers, and retraining the unfrozen layers, wherein subsequent iterations comprise unfreezing upstream layers from a last frozen layer;

train a second artificial intelligence model using a training dataset comprising ECG data including the predetermined set of leads, the second artificial intelligence model being configured to generate artificial ECG data corresponding to each lead of the predetermined set of leads based on the training lead;

record a pairing of the particular device and the second artificial intelligence model to a database of a compatibility service;

input the second ECG data into the trained second artificial intelligence model;

translate, by the second artificial intelligence model, the second ECG data into artificial ECG data corresponding to the leads of the predetermined set of leads; and process, by the first artificial intelligence model, the artificial ECG data to generate one or more predictions regarding the particular cardiac disease state.

9. The computer program product of claim 8, wherein the second artificial intelligence model is trained using a generative adversarial network.

10. The computer program product of claim 8, wherein the one or more predictions include a likelihood of experiencing a cardiac disease state within a predetermined period of time from when the particular device generates the second ECG data.

11. The computer program product of claim 8, wherein the instructions further cause the at least one processor to:

display a notification relating to the one or more predictions on a display screen of the particular device.

12. The computer program product of claim 11, wherein the particular device is wearable by a user.

13. The computer program product of claim 11, wherein the particular device is wearable on a wrist of a user.

14. The computer program product of claim 8, wherein the particular device is wearable around a chest of a user.

15. The computer program product of claim 8, wherein the second number of leads is one lead.

16. The computer program product of claim 8, wherein the standardized plurality of leads comprises 12 leads.

* * * * *